United States Patent [19]

Takatsuna et al.

[11] Patent Number: 4,921,988
[45] Date of Patent: May 1, 1990

[54] PROCESS FOR PREPARING AMINOPROPYL SILANES

[75] Inventors: Kazutoshi Takatsuna, Iruma, Japan; Mamoru Tachikawa, Midland, Mich.; Kouji Shiozawa, Hiki, Japan; Masashi Nakajima, Sendai, Japan; Akihito Shinohara, Kamifukuoka, Japan; Yoshiharu Okumura, Tokyo, Japan

[73] Assignee: Toa Nenryo Kogyo Kabushiki Kaisha, Tokyo, Japan

[21] Appl. No.: 280,727

[22] Filed: Dec. 6, 1988

[30] Foreign Application Priority Data

Dec. 14, 1987 [JP] Japan ................................ 62-316530
Jul. 20, 1988 [JP] Japan ................................ 63-181418

[51] Int. Cl.$^5$ .............................................. C07F 7/10
[52] U.S. Cl. ...................................... 556/413; 556/425; 556/424
[58] Field of Search ........................ 356/413, 415, 424

[56] References Cited

U.S. PATENT DOCUMENTS 4,481,364 11/1984 Chu et al. ............................ 556/413
4,556,722 12/1985 Quirk et al. ......................... 556/413

Primary Examiner—Paul F. Shaver
Attorney, Agent, or Firm—Wenderoth, Lind & Ponack

[57] ABSTRACT

A process for preparing aminopropyl silanes in which an allylamine is reacted with a hydrosilane in the presence of a catalyst comprising (i) metallic rhodium or a rhodium compound and (ii) a basic compound. By the proposed process the corresponding gammaaminopropyl silane can be prepared in a high selectivity and yield within a short period of reaction time.

7 Claims, No Drawings

PROCESS FOR PREPARING AMINOPROPYL SILANES

TECHNICAL FIELD OF THE INVENTION

The present invention relates to a process for preparing aminopropyl silanes such as aminopropyl alkoxy silanes. More particularly, it relates to a process for preparing aminopropyl silanes, in which metallic rhodium or a rhodium compound is used as a catalyst.

BACKGROUND OF THE INVENTION

Silane coupling agents are compounds having in their molecule an organic functional group and a hydrolizable group reactive with inorganic materials. Since the silane coupling agents are, due to their functional groups, capable of chemically bonding an organic polymer with an inorganic material, such as silica, thereby remarkably increasing the mechanical strength of the organic polymer, they are now indispensable in the development of ultrafashionable composite materials.

Aminopropyl silanes such as gamma-aminopropyl alkoxy silanes are used in the art as the silane coupling agent, and it is known that they can be prepared by hydrosililation of an allylamine, which may be substituted on the nitrogen atom, with a hydrosilane.

For example, Japanese Patent Laid-open Publication No. 60-81189 discloses a process for the preparation of aminopropyl alkoxy silanes, which comprises reacting an allylamine with a hydrosilane using a platinum catalyst, such as chloroplatinic acid, in the presence of a promoter, such as anhydrous sodium carbonate. However, the reaction of an allylamine with a hydrosilane in the presence of a platinum catalyst, such as chloroplatinic acid, inevitably produces the corresponding beta-aminopropyl alkoxy silane, which may be referred to herein as the beta-isomer in addition to the desired gamma-aminopropyl alkoxy silane, which may be referred to herein as the gamma-isomer, normally with a ratio of the gamma-isomer to the beta-isomer of from 4 to 6, posing a problem in that the selectivity of the desired gamma-isomer is not satisfactorily high.

Japanese Patent Laid-open Publication No. 61-229,885 discloses a process for the preparation of aminopropyl alkoxy silanes by reacting an allylamine with a hydrosilane in the presence of a catalyst comprising rhodium organic tertiary phosphine complex and optionally triphenylphosphine. By this process gamma-aminopropyl alkoxy silanes can be prepared in a high selectivity. The process is disadvantageous, however, in that a prolonged reaction time is required to achieve a high conversion. Further, an excessive amount of triphenylphosphine must be used to achieve a high selectivity of the gamma-isomer.

J. of Organomet. Chem., 149, 29-36 (1978) deals with the hydrosililation of olefins in the presence of a metallic carbonyl catalyst, such as cobalt-, rhodium-, iridium- and iron-carbonyl compounds and reports that N,N-dimethylaminopropyl triethoxy silane is obtainable in a high yield from N,N-dimethylallylamine and triethoxy silane. It is stated in this article that when an olefinic amine, such as allylamine is hydrosililated, the sililation proceeds preferentially on the amine nitrogen atom. This statement means that hydrosililation of an N-unsubstituted allylamine with a hydrosilane would be unsuitable for the preparation of the corresponding aminopropyl alkoxy silane.

OBJECT OF THE INVENTION

The invention is to solve the problems involved in the prior art and an object of the invention is to provide a process for preparing aminopropyl silanes from a hydrosilane and an allylamine wherein gamma-aminopropyl silanes can be prepared in a high selectivity.

SUMMARY OF THE INVENTION

It has now been found that when an allylamine is reacted with a hydrosilane in the presence of a catalyst comprising (i) metallic rhodium or a rhodium compound and (ii) a basic compound, the desired gamma-aminopropyl silanes can be prepared in a high yield and within a shortened reaction time.

Thus, a process for preparing aminopropyl silanes according to the invention comprises reacting an allylamine of the formula [I]

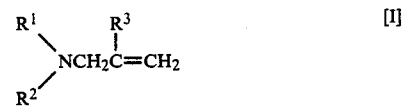

wherein $R^1$ and $R^2$, each represents hydrogen, alkyl having from 1 to 10 carbon atoms, alkenyl having from 2 to 10 carbon atoms, phenyl, substituted phenyl, $-CH_2CH_2NHCH_2CH_2NH_2$ or $-CH_2CH_2NH_2$, and $R^3$ is hydrogen or alkyl having from 1 to 6 carbon atoms with a hydrosilane in the presence of a catalyst comprising (i) metallic rhodium or a rhodium compound and (ii) a basic compound.

DETAILED DESCRIPTION OF THE INVENTION

A process for preparing aminopropyl silanes according to the invention will be fully described hereinafter.

ALLYLAMINES

Allylamines represented by the formula [I] above can be used in the process according to the invention for preparing aminopropyl silanes.

Examples of such allylamines include, for example, allylamine, N,N-dimethyallylamine, N,N-diethylallylamine, N-methylallylamine, N-ethylallylamine, 2-methylallylamine, diallylamine, allylethylenediamine, and N-allylaniline.

HYDROSILANES

In the process according to the invention the allylamine as described above is reacted with a hydrosilane. Hydrosilanes are compounds having at least one Si—H linkage in the molecule and may be represented by the following formulas [II], [III] or [IV]:

wherein $R^4$, $R^5$ and $R^6$ are the same or different and each represents alkyl or alkoxy;

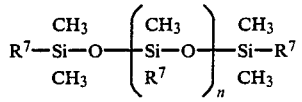  [III]

wherein each $R^7$ represents hydrogen or methyl with the proviso that at least one $R^7$ represents hydrogen, and n is an integer from 0 to 300; and

  [IV]

wherein m is an integer from 3 to 10.

Examples of hydrosilanes of the formulas [II], [III] and [IV] include, for example, triethoxy silane, trimethoxy silane, trimethylsilane, triethylsilane, tripropoxy silane, tributoxy silane, methyl dimethoxy silane, ethyl dimethoxy silane, methyl diethoxy silane, dimethyl methoxy silane, trioctyloxy silane, methyl dioctyloxy silane, dimethyl octyloxy silane, 1,1,3,3-tetramethyldisiloxane, pentamethyldisiloxane, alpha, omega-dihydropolysiloxane, polysiloxanes having at least one Si—H linkage in the polymer chain, 1,3,5,7-tetramethyl-cyclotetrasiloxane and 1,3,5,7,9-pentamethyl-cyclopentasiloxane.

RHODIUM COMPOUNDS

When an allylamine as described above is reacted with a hydrosilane as described above according to the invention, use is made of a catalyst comprising (i) metallic rhodium or a rhodium compound and (ii) a basic compound.

Usable rhodium compounds include monovalent, divalent, trivalent and zero valent rhodium complexes and other rhodium compounds than rhodium complexes.

Anionic ligand possessed by mono-, di- and tri-valent rhodium complexes may be selected from halogen such as chlorine, bromine and iodine, alkyl, acetoxy, alkoxy, acetylacetone, hydroxy, hydride and phosphide.

Other ligand sites of rhodium may be occupied by neutral ligands including, for example, ethylene, propylene, cyclooctene, norbornene and other monoolefins; 1,3-butadiene, 1,3-pentadiene, 1,3-cyclohexadiene and other conjugated dienes; 1,5-cyclooctadiene, norbornadiene, 1,4-pentadiene, dicyclopentadiene and other nonconjugated dienes; aromatic amines such as pyridine, dipyridyl and ortho-phenanthroline; nitrile, isonitrile, carbonyl and phosphine.

MONOVALENT RHODIUM COMPLEXES

Examples of monovalent rhodium complexes include, for example,
di-μ-methoxybis(1,5-cyclooctadiene) dirhodium [Rh(μ-OMe)(1,5-COD)]$_2$,
di-μ-hydroxybis(1,5-cyclooctadiene) dirhodium [Rh(μ-OH)(1,5-COD)]$_2$,
di-μ-methoxybis(1,5-tetrafluorobenzovarelene) dirhodium [Rh(μ-OMe)(1,5-TFB)]$_2$,
[rhodium(1,5-cyclooctadiene)(indole)] perchlorate [Rh(1,5-COD)(Indole)] ClO$_4$,
di-μ-chlorobis(1,5-cyclooctadiene) dirhodium [Rh(μ-Cl)(1,5-COD)]$_2$.
di-μ-bromobis(1,5-cyclooctadiene) dirhodium [Rh(μ-Br)(1,5-COD)]$_2$,
di-μ-iodobis(1,5-cyclooctadiene) dirhodium [Rh(μ-I)(1,5-COD)]$_2$,
di-μ-chlorobis(1,5-hexadiene) dirhodium [Rh(μ-Cl)(1,5-C$_6$H$_{10}$)]$_2$,
di-μ-chlorotetrakis(2,3-dimethyl-2-butene) dirhodium [Rh(μ-Cl)(C$_6$H$_{12}$)$_2$]$_2$,
di-μ-chlorotetrakisethene dirhodium [Rh(μ-Cl)(C$_2$H$_4$)$_2$]$_2$,
acetylacetonatobis(ethylene) rhodium Rh(acac)(C$_2$H$_4$)$_2$,
di-μ-chlorotetracarbonyl dirhodium [Rh(μ-Cl)(CO)$_2$]$_2$,
di-μ-acetoxybis(1,5-cyclooctadiene) dirhodium [Rh(μ-OAc)(1,5-COD)]$_2$,
bis(1,5-cyclooctadiene)di-μ-peroxydirhodium [Rh(μ-O)(1,5-COD)]$_2$,
cyclopentadienyl(1,5-cyclooctadiene)rhodium Rh(CPD)(1,5-COD),
acetylacetonato(1,5-cyclooctadiene)rhodium Rh(acac)(1,5-COD),
di-μ-chlorobis(1,5-cyclooctatetraene) dirhodium [Rh(μ-Cl)(1,5-COT)]$_2$,
di-μ-chlorobis(di-cyclopentadiene) dirhodium [Rh(μ-Cl)(DCPD)]$_2$,
di-μ-phenoxybis(1,5-cyclooctadiene) dirhodium [Rh(μ-OPh)(1,5-COD)]$_2$,
benzoylacetonato(1,5-cyclooctadiene) rhodium Rh(bzac)(1,5-COD),
di-benzoylmethanato(1,5-cyclooctadiene) rhodium Rh(db m)(1,5-COD),
di-μ-chlorobis(norbornadiene) dirhodium [Rh(μ-Cl)(NBD)]$_2$,
di-μ-acetoxybis(norbornadiene) dirhodium [Rh(μ-OAc)(NBD)]$_2$,
a trimer of bis(1,5-cyclooctadiene) μ-carbonate dirhodium Rh$_6$(1,5-COD)$_6$(CO$_3$)$_3$,
hydridocarbonyltris(triphenylphosphine) rhodium HRh(CO)(PPh$_3$)$_3$,
hydridotetrakis(triphenylphosphine)rhodium HRh(PPh$_3$)$_4$,
chlorotris(triphenylphosphine) rhodium RhCl(PPh$_3$)$_3$,
and di-μ-diphenylphosphidebis(1,5-COD) dirhodium [Rh(μ-PPh$_2$)(1,5-COD)]$_2$.

DIVALENT RHODIUM COMPLEXES

Examples of divalent rhodium complexes include, for example,
tetrakis(μ-acetato) dirhodium [Rh(OAc)$_2$]$_2$,
bis(pentamethylcyclopentadienyl) rhodium Rh(η$^5$-C$_5$Me$_5$)$_2$,
chlorobis(dipyridyl)rhodium [Rh(dipy)$_2$Cl]$^+$,
and tetrakis(μ-acetato)bistriphenylphosphine dirhodium [PPh$_3$Rh(OAc)$_2$]$_2$.

TRIVALENT RHODIUM COMPLEXES

Examples of trivalent rhodium complexes include, for example,
hexachlororhodium [RhCl$_6$]$^{3-}$,
trichlorotris(triethylphosphine) rhodium RhCl$_3$(PEt$_3$)$_3$,
and di-μ-chlorotetra-π-allyl dirhodium [Rh(μ-Cl) (π-C$_3$H$_5$)$_2$]$_2$.

ZEROVALENT RHODIUM COMPLEXES

In zerovalent rhodium complexes all of the ligand sites of rhodium are occupied by neutral ligands as described above. Examples of zerovalent rhodium complexes include, for example,
dirhodium octacarbonyl Rh$_2$(CO)$_8$,
tetrarhodium dodecacarbonyl Rh$_4$(CO)$_{12}$,
hexarhodium hexadecacarbonyl Rh$_6$(CO)$_{16}$, and hexarhodium tetradecacarbonyl(norbornadiene) $Rh_6(CO)_{14}(NBD)$.

OTHER RHODIUM COMPOUNDS

Examples of rhodium compounds other than rhodium complexes which can be used herein include rhodium halides such as $RhCl_3 \cdot nH_2O$, $RhBr_3$ and $RhI_3$.

BASIC COMPOUNDS

In the process according to the invention use is made of a catalyst comprising (i) metallic rhodium or the rhodium compound as described above and (ii) a basic material which is (a) an alkali metal, an alkaline earth metal or (b) a basic compound containing at least one nitrogen atom and which may be a basic electron doner, a Lewis base or a basic reducing agent.

BASIC ELECTRON DONER

The basic electron doners may be halogen, chalcogen, Group VA(N.P. As, Sb and Bi), Group IVA (C, Si, Ge, Sn and Pb) and Group IIIA(B, Al, Ga, In and Tl) compounds of alkali metals, alkaline earth metals, Group IIIA metals and oniums of Group VA elements Examples of such basic electron doners which can be used herein include, for example, potassium fluoride, rubidium fluoride, cesium fluoride, lithium fluoride, sodium fluoride, barium fluoride, magnesium fluoride, tetrabutylammonium fluoride, lithium oxide, sodium oxide, potassium oxide, rubidium oxide, cesium oxide, lithium hydroxide, sodium hydroxide, potassium hydroxide, rubidium hydroxide, cesium hydroxide, barium hydroxide, diethylaluminum hydroxide, tetrabutylammonium hydroxide, lithium methoxide, lithium ethoxide, lithium propoxide, lithium butoxide, sodium methoxide, sodium ethoxide, potassium methoxide, potassium ethoxide, rubidium ethoxide, cesium ethoxide, triethylammonium methoxide, sodium triphenylsilanolate ($NaOSiPh_3$), lithium triphenylsilanolate ($LiOSiPh_3$), sodium triethylgermylate ($NaOGeEt_3$), potassium tributylstannylate ($KOSnBu_3$), sodium phenoxide, diethylaluminum methoxide, sodium carbonate, potassium acetate, sodium sulfite, sodium nitrite, sodium hypochlorite, potassium chlorite, sodium chlorate, sodium perchlorate, potassium cyanate, sodium thiocyanate, lithium hydrosulfide (LiSH), sodium hydrosulfide (NaSH), potassium hydrosulfide (KSH), sodium azide, sodiumamide ($H_2NNa$), potassium diethylamide, sodium diphenylphosphide ($Ph_2PNa$), n-butyllithium, phenyllithium, isopropylmagnesium chloride, phenylmagnesium bromide, diphenylmethylsilyllithium, triphenylgermyllithium, tributylstannyllithium and sodium tetrafluoroborate.

LEWIS BASES

Examples of the Lewis bases which can be used herein include, for example, hydroxylamine, hydrazine, phenylhydrazine, diazabicyclo[2,2,2] octane, acetoaldoxime ($CH_3CH=NOH$), triethylamine, quinuclidine and pyrrolidine.

BASIC REDUCING AGENTS

The basic reducing agents may be hydrides of alkali metals, alkaline earth metals, Group IIIA metals and Group IVA elements as well as alkali metals and alkaline earth metals.

Examples of such basic reducing agents which can be used herein include, for example, lithium hydride, calcium hydride, lithium aluminum hydride, sodium borohydride, lithium tri-tert-butoxyaluminum hydride, lithium triethyl borohydride, tributylgermanium hydride, tributyltin hydride, sodium tri-tert-butoxy borohydride, lithium metal, sodium metal, potassium metal, rubidium metal, cesium metal, beryllium metal, magnesium metal and calcium metal.

The basic compound is used in such an amount that from 0.1 to 30 moles, preferably from 0.2 to 5 moles of the basic compound, per mole of the rhodium metal or rhodium compound, may be present in the reaction system. With substantially less than the above-prescribed amount of the basic compound, a satisfactory catalytic activity will not be realized. Whereas when an unduly excessive amount of the basic compound is used, increasing amounts of by-products tend to be formed due to disproportionation of the hydrosilane reactant.

It is also possible to add such an additional amount of the basic compound to the reaction system during or after the reaction so that the total amount of the basic compound is within the above-prescribed range, thereby keeping the catalytic activity at a high level.

The basic compound may be added to the reaction system as such (in solid) or in the form of a solution in an appropriate solvent such as ethanol, DMSO or 18-crown-6-ether.

REACTION CONDITIONS

The allylamine and hydrosilane are preferably used in such amounts that a ratio of the allylamine to the hydrosilane by mole is within the range from about 1.3:1 to about 1:1.3.

The allylamine and hydrosilane are used in the reaction according to the invention preferably after having impurities such as halogen, sulfur and phosphorus compounds removed as far as possible.

The reaction may be carried out under atmospheric or elevated pressure. The reaction is carried out at a temperature of not lower than 15° C., preferably from about 50° C. to about 250° C., more preferably from about 70° C. to about 200° C. If a reaction temperature substantially below 15° C. is used, the desired gamma-aminopropyl silanes will be formed in little amounts. Whereas, when the reaction temperature increases above 250° C., increasing amounts of the beta-isomer tend to be formed, undesirably lowering the selectivity of the gamma-isomer.

While the rhodium metal or compound may be used in an excess amount, it is sufficient for it to be present in the reaction system in an amount on the order of from $10^{-6}$ to $10^{-3}$ mole per mole of the allylamine, on a rhodium basis.

In carrying out the reaction, solvents may or may not be used. When solvents are used, generally, hydrocarbon solvents, such as toluene, xylene, heptane, dodecane, ditolylbutane and cumene are preferred.

When a rhodium complex is employed as the rhodium compound, it is frequently advantageous to carry out the reaction in the presence of excess amounts of an neutral ligand compound which may be the same as or different from neutral ligands of the employed rhodium complex.

While the reaction time greatly depends upon the reaction temperature used, it may normally be within the range between about 0.5 and about 2.0 hours.

When an allylamine is reacted with a hydrosilane in the presence of a catalyst comprising (i) metallic rhodium or a rhodium compound and (ii) a basic compound in accordance with the invention, we have found as shown in the following examples, that the corresponding gamma-aminopropyl silanes can be produced in a high selectivity with little yield of the beta-isomer, leading to a high gamma/beta ratio. Further, the reaction rapidly proceeds, and thus, the gamma-isomer can be obtained in a yield as high as 75% or higher.

In contrast, if an allylamine is reacted with a hydrosilane, using a chloroplatinic acid catalyst, the yield of the gamma-isomer is on the order of 40–50%, with a gamma/beta ratio of about 4. Further, if an allylamine is reacted with a hydrosilane, using a catalyst consisting solely of hydridocarbonyl tris(triphenylphosphine) rhodium complex as a catalyst, the gamma-isomer with a gamma/beta ratio of about 60 can only be obtained at the cost of a prolonged reaction time, e.g., 6 hours or more, owing to a slow reaction rate.

EFFECTS OF THE INVENTION

By a process for preparing aminopropyl silanes according to the invention, in which an allylamine is reacted with a hydrosilane in the presence of a catalyst comprising (i) metallic rhodium or a rhodium compound and (ii) a basic compound, the corresponding gamma-aminopropyl silanes can be prepared in a high selectivity and yield within a short period of reaction time.

While the invention is illustrated by the following examples, the invention is not limited thereto.

EXAMPLE 1

A three-neck flask equipped with a reflux condenser, stirrer and thermometer, was charged with 0.066 g of rhodium trichloride trihydrate, $RhCl_3.3H_2O$ (0.1 mole % of Rh per mole of triethoxysilane), 0.060 g of sodium hydroxide powder and 50 ml of xylene. The mixture was heated to a temperature of 130° C. under stirring by placing the flask on an oil bath maintained at a temperature of 130° C. To the heated mixture a mixture of 41 g of triethoxy silane (0.25 mole) and 14 g of allylamine (0.25 mole) was dropwise added over a period of about one hour.

After completion of the reaction the reaction mixture was subjected to gas chromatography analysis. It was revealed that gamma-aminopropyl triethoxy silane had been formed in a yield of 90% on a triethoxysilane basis, while the yield of beta-aminopropyl triethoxy silane was less than 0.2%.

EXAMPLES 2 TO 47

The reaction and analysis of Example 1 were repeated except that the rhodium compound, basic compound, solvent and/or reaction temperature indicated in Table 1 were used. Results are shown in Table 1, in which the indicated yields are based on the triethoxysilane.

TABLE 1

|  | Rh compound (g) | Basic compound (g) | Solvent (ml) | Temp. (°C.) | yield (%) of α-isomer | yield (%) of β-isomer |
|---|---|---|---|---|---|---|
| Example 2 | $RhCl_3.3H_2O$ (0.066) | LiOH (0.018) | xylene (50) | 130 | 90 | <0.2 |
| Example 3 | $RhBr_3$ (0.086) | NaOH (0.03) | xylene (50) | 130 | 85 | <0.2 |
| Example 4 | $RhBr_3$ (0.043) | $Ba(OH)_2$ (0.06) | xylene (50) | 100 | 60 | <0.2 |
| Example 5 | $[Rh(\mu-Cl)(\pi-C_3H_5)_2]_2$ (0.045) | KOH (0.046) | xylene (50) | 120 | 90 | <0.2 |
| Example 6 | $[Rh(\mu-Br)(DCPD)]_2$ (0.080) | NaOH (0.04) | cumene (50) | 130 | 90 | <0.2 |
| Example 7 | $[Rh(\mu-OH)(1,5-COD)]_2$ (0.062) | RbOH (0.05) | xylene (50) | 120 | 90 | <0.2 |
| Example 8 | $[Rh(\mu-Cl)(\pi-C_3H_5)_2]_2$ (0.045) | CsOH (0.075) | xylene (50) | 120 | 90 | <0.2 |
| Example 9 | $[Rh(\mu-Cl)(NBD)]_2$ (0.058) | NaOEt (0.085) | xylene (50) | 120 | 90 | <0.2 |
| Example 10 | $[Rh(\mu-Br)(NBD)]_2$ (0.069) | LiOH (0.025) | ditolylbutane (50) | 130 | 85 | <0.2 |
| Example 11 | $[Rh(\mu-Cl)(CO)_2]_2$ (0.024) | $NaOSiPh_3$ (0.075) | xylene (50) | 120 | 80 | <0.2 |
| Example 12 | $[Rh(\mu-OMe)(1,5-COD)]_2$ (0.006) | NaOMe (0.0014) | xylene (50) | 120 | 85 | <0.2 |
| Example 13 | $[Rh(\mu-Cl)(1,5-COD)]_2$ (0.062) | LiOEt (0.018) | xylene (50) | 130 | 90 | <0.2 |
| Example 14 | $Rh_4(CO)_{12}$ (0.047) | KOEt (0.042) | xylene (50) | 120 | 80 | <0.2 |
| Example 15 | $[Rh(1,5-COD)_2]BF_4$ (0.10) | NaOH (0.03) | xylene (50) | 120 | 86 | <0.2 |
| Example 16 | $HRh(CO)(PPh_3)_3$ (0.23) | NaOH (0.03) | xylene (50) | 120 | 90 | <0.2 |
| Example 17 | $RhCl(PPh_3)_3$ (0.23) | NaOH (0.03) | xylene (50) | 130 | 90 | <0.2 |
| Example 18 | $[Rh(\mu-Me)(1,5-COD)]_2$ (0.057) | NaOMe (0.014) | none | 120 | 85 | <0.2 |
| Example 19 | $Rh(acac)(1,5-COD)$ (0.078) | KOH (0.056) | xylene (50) | 130 | 90 | <0.2 |
| Example 20 | $RhCl_3.3H_2O$ (0.066) | NaSH (0.084) | xylene (50) | 110 | 80 | <0.2 |
| Example 21 | $RhCl_3.3H_2O$ (0.066) | n-BuLi (0.032) | xylene (50) | 110 | 70 | <0.2 |
| Example 22 | $RhCl_3.3H_2O$ (0.0066) | i-PrMgCl (0.0051) | xylene (50) | 110 | 60 | <0.2 |
| Example 23 | $RhCl_3.3H_2O$ (0.066) | $NaNH_2$ (0.029) | none | 120 | 70 | <0.2 |
| Example 24 | $RhCl_3.3H_2O$ | $LiPPh_2$ | xylene | 110 | 60 | <0.2 |

TABLE 1-continued

|  | Rh compound (g) | Basic compound (g) | Solvent (ml) | Temp. (°C.) | yield (%) of α-isomer | β-isomer |
|---|---|---|---|---|---|---|
|  | (0.066) | (0.14) | (50) |  |  |  |
| Example 25 | RhCl$_3$.3H$_2$O (0.066) | KF* (0.044) | xylene (50) | 100 | 60 | <0.2 |
| Example 26 | RhCl$_3$.3H$_2$O (0.066) | LiH (0.004) | xylene (50) | 110 | 80 | <0.2 |
| Example 27 | RhCl$_3$.3H$_2$O (0.066) | CaH$_2$ (0.016) | xylene (50) | 110 | 80 | <0.2 |
| Example 28 | RhCl$_3$.3H$_2$O (0.066) | LiAlH$_4$ (0.019) | xylene (50) | 120 | 85 | <0.2 |
| Example 29 | RhCl$_3$.3H$_2$O (0.066) | NaBH$_4$ (0.014) | xylene (50) | 120 | 80 | <0.2 |
| Example 30 | RhCl$_3$.3H$_2$O (0.066) | NaB(tert.-OBu)$_3$H (0.19) | xylene (50) | 110 | 70 | <0.2 |
| Example 31 | RhCl$_3$.3H$_2$O (0.066) | Bu$_3$SnH (0.22) | xylene (50) | 110 | 70 | <0.2 |
| Example 32 | RhCl$_3$.3H$_2$O (0.066) | H$_2$N-NH$_2$ (0.032) | xylene (50) | 100 | 70 | <0.2 |
| Example 33 | RhCl$_3$.3H$_2$O (0.066) | NH$_2$OH (0.041) | xylene (50) | 100 | 70 | <0.2 |
| Example 34 | RhCl$_3$.3H$_2$O (0.066) | N(Et)$_3$ & cathecol (0.076) (0.083) | xylene (50) | 100 | 70 | <0.2 |
| Example 35 | [Rh(μ-Cl)(1,5-COD)]$_2$ (0.062) | KOH (0.056) | xylene (50) | 130 | 90 | <0.2 |
| Example 36 | [Rh(μ-Br)(DCPD)]$_2$ & DCPD (0.080) (3.3) | NaOH (0.04) | xylene (50) | 130 | 90 | <0.2 |
| Example 37 | [Rh(μ-Cl)(1,5-COD)]$_2$ & 1,5-COD (0.062) (2.76) | KOH (0.07) | xylene (50) | 130 | 85 | <0.2 |
| Example 38 | [Rh(μ-Cl)(1,5-COD)]$_2$ (0.062) | NaOH (0.04) | xylene (50) | 130 | 90 | <0.2 |
| Example 39 | [Rh(μ-Cl)(NBD)]$_2$ (0.058) | LiOH (0.012) | xylene (50) | 130 | 80 | <0.2 |
| Example 40 | [Rh(μ-OMe)(1,5-COD)]$_2$ (0.006) | CsF (0.038) | xylene (50) | 120 | 90 | <0.2 |
| Example 41 | Active C carry 'g 5 wt % Rh (0.515) | NaOEt (0.034) | xylene (100) | 100 | 80 | <0.2 |
| Example 42 | RhCl$_3$.3H$_2$O (0.066) | Li (0.0035) | xylene (50) | 110 | 80 | <0.2 |
| Example 43 | RhCl$_3$.3H$_2$O (0.033) | Na (0.0086) | xylene (50) | 120 | 85 | <0.2 |
| Example 44 | RhCl$_3$.3H$_2$O (0.033) | K (0.015) | none | 120 | 80 | <0.2 |
| Example 45 | [Rh(μ-Cl)(CO)$_2$]$_2$ (0.024) | Mg (0.030) | xylene (50) | 100 | 70 | <0.2 |
| Example 46 | [Rh(μ-PPh$_2$)(1,5-COD)]$_2$ (0.099) | NaOH (0.030) | none | 110 | 80 | <0.2 |
| Example 47 | [Rh(μ-OH)(1,5-COD)]$_2$ (0.057) | n-Bu$_4$NF (0.20) | xylene (50) | 110 | 90 | <0.2 |

*solibilized with 18-crown-6-ether

EXAMPLE 48

The reaction was carried out as in Example 1 except that 30.5 g of trimethoxysilane (0.25 mole) was used instead of the triethoxysilane.

After completion of the reaction the reaction mixture was subjected to gas chromatography analysis. It was revealed that gamma-aminopropyl trimethoxy silane had been formed in a yield of 87% on a trimethoxysilane basis, while the yield of beta-isomer was less than 0.2%.

EXAMPLE 49

The reaction was carried out as in Example 1 except that 29.0 g of triethylsilane (0.25 mole) was used instead of the triethoxysilane.

After completion of the reaction the reaction mixture was subjected to gas chromatography analysis. It was revealed that gamma-aminopropyltriethyl silane had been formed in a yield of 80% on a triethylsilane basis, while the yield of beta-isomer was less than 0.2%.

EXAMPLE 50

The reaction was carried out as in Example 1 except that 16.8 g of 1,1,3,3-tetramethyldisiloxane (0.125 mole) was used instead of the triethoxysilane.

After completion of the reaction the reaction mixture was subjected to gas chromatography analysis. It was revealed that 1,3-bis-gamma-aminopropyl 1,1,3,3,-tetradimethyldisiloxane had been formed in a yield of 70% on a 1,1,3,3,-tetramethyldisiloxane basis, while the yield of beta-isomer was less than 0.2%.

EXAMPLE 51

The reaction was carried out as in Example 1 except that 30.5 g of trimethoxysilane (0.25 mole) was used instead of the triethoxysilane and that 0.062 g of [Rh(μ-Cl)(1,5-COD)]$_2$ (0.1 mole % of Rh per mole of trimethoxysilane) and 0.056 g of KOH were used instead of the rhodium and basic compounds of Example 1, respectively.

After completion of the reaction the reaction mixture was subjected to gas chromatography analysis. It was revealed that gamma-aminopropyl trimethoxy silane had been formed in a yield of 80% on a trimethoxysilane basis, while the yield of beta-isomer was less than 0.2%.

EXAMPLE 52

The reaction was carried out as in Example 1 except that 25.0 g of allylethylenediamine (0.25 mole) was used instead of the allylamine.

After completion of the reaction the reaction mixture was subjected to gas chromatography analysis. It was revealed that N-(2-aminoethyl)-3-aminopropyl triethoxy silane had been formed in a yield of 80% on a triethoxysilane basis, while the yield of beta-isomer was less than 0.2%.

EXAMPLE 53

The reaction was carried out as in Example 1 except that 25.0 g of allylethylenediamine (0.25 mole) was used instead of the allylamine and that 0.062 g of [Rh($\mu$-Cl)(1,5-COD)]$_2$ (0.1 mole % of Rh per mole of triethoxysilane) and 0.056 g of KOH were used instead of the rhodium and basic compounds of Example 1, respectively.

After completion of the reaction the reaction mixture was subjected to gas chromatography analysis. It was revealed that N-(2-aminoethyl)-3-aminopropyl triethoxy silane had been formed in a yield of 80% on a triethoxysilane basis, while the yield of beta-isomer was less than 0.2%.

COMPARATIVE EXAMPLE 1

The procedure of Example 1 was repeated except that 0.062 g of [Rh($\mu$-Cl)(1,5-COD)]$_2$ (0.1 mole % of Rh per mole of triethoxysilane) was used instead of the rhodium compound of Example 1 and no basic compound was used.

It was revealed by gas chromatography that gamma-aminopropyl triethoxy silane had been formed in a yield of 1% or less.

COMPARATIVE EXAMPLE 2

The procedure of Example 1 was repeated except that 0.056 g of KOH was used instead of the NaOH of Example 1 and no rhodium metal nor compound was used.

It was revealed by gas chromatography that gamma-aminopropyl triethoxy silane had been formed not at all and that the reaction mixture primarily comprised of triethoxysilane.

COMPARATIVE EXAMPLE 3

The procedure of Example 1 was repeated except that 0.74 g of RhCl(PPh$_3$)$_3$ (1.0 mole % of Rh per mole of triethoxysilane) was used instead of the rhodium compound of Example 1 and no basic compound was used.

It was revealed by gas chromatography that gamma-aminopropyl triethoxy silane had been formed in a yield of 1% or less.

What is claimed is:

1. A process for preparing aminopropyl silanes which comprises reacting an allylamine of the formula

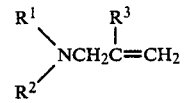
[1]

wherein $R^1$ and $R^2$, each represents hydrogen, alkyl having from 1 to 10 carbon atoms, alkenyl having from 2 to 10 carbon atoms, phenyl, substituted phenyl, —CH$_2$CH$_2$NHCH$_2$CH$_2$NH$_2$ or —CH$_2$CH$_2$NH$_2$, and $R^3$ is hydrogen or alkyl having from 1 to 6 carbon atoms with a hydrosilane in the presence of a catalyst comprising (i) metallic rhodium or a rhodium compound and (ii) a basic material which is (a) an alkali metal, an alkaline earth metal or a basic compound thereof or (b) a basic compound containing at least one nitrogen atom.

2. The process in accordance with claim 1 wherein said catalyst comprises (i) a metallic rhodium or a rhodium compound and (ii) from 0.1 to 30 moles, per mole of rhodium, of a basic material which is (a) an alkali metal, an alkaline earth metal or a basic compound thereof or (b) a basic compound containing at least one nitrogen atom.

3. The process in accordance with claim 1 wherein said rhodium compound is selected from di-$\mu$-methoxybis(1,5-cyclooctadiene) dirhodium, di-$\mu$-hydroxybis(1,5-cyclooctadiene) dirhodium, di-$\mu$-methoxybis(1,5-tetrafluorobenzovarelene) dirhodium, [rhodium(1,5-cyclooctadiene)(indole)] perchlorate, di-$\mu$-chlorobis(1,5-cyclooctadiene) dirhodium, di-$\mu$-bromobis(1,5-cyclooctadiene) dirhodium, di-$\mu$-iodobis(1,5-cyclooctadiene) dirhodium, di-$\mu$-chlorobis(1,5-hexadiene) dirhodium, di-$\mu$-chlorotetrakis(2,3-dimethyl-2-butene) dirhodium, di-$\mu$-chlorotetrakisethene dirhodium, acetylacetonatobis(ethylene) rhodium, di-$\mu$-chlorotetracarbonyl dirhodium, di-$\mu$-acetoxybis(1,5-cyclooctadiene) dirhodium, bis(1,5-cyclooctadiene)di-$\mu$-peroxydirhodium, cyclopentadienyl(1,5-cyclooctadiene)rhodium, acetylacetonato(1,5-cyclooctadiene)rhodium, di-$\mu$-chlorobis(1,5-cyclooctatetraene) dirhodium, di-$\mu$-chlorobis(dicyclopentadiene) dirhodium, di-$\mu$-phenoxybis(1,5-cyclooctadiene) dirhodium, benzoylacetonato(1,5-cyclooctadiene) rhodium, di-benzoylmethanato(1,5-cycloctadiene) rhodium, di-$\mu$-chlorobis(norbornadiene) dirhodium, di-$\mu$-acetoxybis(norbornadiene) dirhodium, a trimer of bis(1,5-cyclooctadiene) $\mu$-carbonate dirhodium, hydridocarbonyltris(triphenylphosphine) rhodium, hydridotetrakis(triphenylphosphine)rhodium, chlorotris(triphenylphosphine) rhodium, di-$\mu$-diphenylphosphidebis(1,5-COD) dirhodium, tetrakis($\mu$-acetato) dirhodium, bis(pentamethylcyclopentadienyl) rhodium, chlorobis(dipyridyl)rhodium, tetrakis($\mu$-acetato)bistriphenylphosphine dirhodium, hexachlororhodium, trichlorotris(triethylphosphine) rhodium, di-$\mu$-chlorotetra-$\pi$-allyl dirhodium, dirhodium octacarbonyl, tetrarhodium dodecacarbonyl, hexarhodium hexadecacarbonyl, hexarhodium tetradecacarbonyl(norbornadiene), rhodium trichloride trihydrate, rhodium tribromide and rhodium triiodide.

4. The process in accordance with claim 1 in which the basic material is an alkali metal.

5. The process in accordance with claim 1 in which the basic material is an alkaline earth metal.

6. The process in accordance with claim 1 in which the basic material is an alkali metal and alkaline earth metal compound.

7. The process in accordance with claim 1 in which the basic material is a Lewis base containing at least one nitrogen atom.

* * * * *